US006716616B1

(12) United States Patent
Donoho et al.

(10) Patent No.: US 6,716,616 B1
(45) Date of Patent: Apr. 6, 2004

(54) HUMAN KINASE PROTEINS AND POLYNUCLEOTIDES ENCODING THE SAME

(75) Inventors: Gregory Donoho, The Woodlands, TX (US); C. Alexander Turner, Jr., The Woodlands, TX (US); Michael C. Nehls, Stockdorf (DE); Glenn Friedrich, Houston, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 576 days.

(21) Appl. No.: 09/671,050

(22) Filed: Sep. 27, 2000

Related U.S. Application Data

(60) Provisional application No. 60/156,511, filed on Sep. 28, 1999.

(51) Int. Cl.[7] .......................... C12N 1/20; C12N 15/00; C12N 5/00; C12Q 1/68; C07H 21/02
(52) U.S. Cl. .................. 435/252.3; 435/194; 435/6; 435/320.1; 435/325; 536/23.2
(58) Field of Search .................. 536/23.2; 435/194, 435/320.1, 325, 6, 252.3, 144

(56) References Cited

U.S. PATENT DOCUMENTS

| | | | |
|---|---|---|---|
| 4,215,051 A | 7/1980 | Schroeder et al. | 260/346.7 |
| 4,376,110 A | 3/1983 | David et al. | 436/513 |
| 4,946,778 A | 8/1990 | Ladner et al. | 435/69.1 |
| 5,817,479 A | 10/1998 | Au-Young et al. | 435/69.1 |
| 5,830,721 A | 11/1998 | Stemmer et al. | 435/172.1 |
| 5,837,458 A | 11/1998 | Minshull et al. | 435/6 |
| 5,869,336 A | 2/1999 | Meyer et al. | 435/348 |
| 5,877,397 A | 3/1999 | Lonberg et al. | 800/2 |
| 6,075,181 A | 6/2000 | Kucherlapati et al. | 800/25 |

FOREIGN PATENT DOCUMENTS

WO    WO 00/73469 A2    12/2000

OTHER PUBLICATIONS

EST Database, Accession No. AA626859, Oct. 1997.*
Bird et al, 1988, "Single–Chain Antigen–Binding Proteins", Science 242:423–426.
Bitter et al, 1987, "Expresssion and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.
Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Greenspan et al, 1993, "Idiotypes: structure and immunogenicity", FASEB Journal 7:437–444.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in Escherichia coli", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985, "Up–promoter mutations in the Ipp gene of Escherichia coli", Nucleic Acids Research 13(9):3101–3110.
Janknecht et al, 1991, "Rapid and efficient purification of native histidine–tagged protein expressed by recombinant vaccinia virus", PNAS USA 88:8972–8976.
Kohler & Milstein, 1975, "Continuous cultures of fused cells secreting antibody of predefined specificity", Nature 256:495–497.
Logan et al, 1984, "Adenovirus tripartite leader sequence enhances translation of mRNAs late after infection", Proc. Natl. Acad. Sci. USA 81:3655–3659.
Lowy et al, 1980, "Isolation of Transforming DNA: Cloning the Hamster aprt Gene", Cell 22:817–823.
Morrison et al, 1984, "Chimeric human antibody molecules: Mouse antigen–binding domains with human constant region domains", Proc. Natl. Acad. Sci. USA 81:6851–6855.
Mulligan & Berg, 1981, "Selection for animal cells that express the Escherichia coli gene coding for xanthine–guanine phosphoribosyltransferase", Proc. Natl. Acad. Sci. USA 78(4):2072–2076.
Neuberger et al, 1984, "Recombinant antibodies possessing novel effector functions", Nature 312:604–608.
Nisonoff, 1991, "Idiotypes: Concepts and Applications", J. of Immunology 147:2429–2438.
O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.
Ruther et al, 1983, "Easy identification of cDNA clones", EMBO Journal 2(10):1791–1794.
Santerre et al, 1984, "Expression of prokaryotic gene for hygromycin B and G418 resistance as dominant–selection markers in mouse L cells", Gene 30:147–156.
Sarin et al, 1988, "Inhibition of acquired immunodeficiency syndrome virus by oligodeoxynucleoside methylphosphonates", Proc. Natl. Acad. Sci. USA 85:7448–7451.

(List continued on next page.)

Primary Examiner—Maryam Monshipouri

(57) ABSTRACT

Novel human polynucleotide and polypeptide sequences are disclosed that can be used in therapeutic, diagnostic, and pharmacogenomic applications.

10 Claims, No Drawings

OTHER PUBLICATIONS

Smith et al, 1983, "Molecular Engineering of the Autographa californica Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1980, "Transformation of mammalian cells with an amplifiable dominant–acting gene", Proc. Natl. Acad. Sci. USA 77(6):3567–3570.

Wigler et al, 1977, "Transfer of Purified Herpes Virus Thymidine Kinase Gene to Cultured Mouse Cells", Cell 11:223–232.

Hillier et al.: "zu89f10.s1 Soares–testis–NHT *Homo sapiens* cDNA clone Image: 745195 3' similar to SW:KKIA_Human Q00532 Serinethreonine–Protein Kinase KKIALRE" EMBL Sequence Database Oct. 28, 1997, XP002161432. Heidelberg DE Ac AA626859.

Doe Joint Genome Institute: "Sequencing of human chromosome 16" EMBL Sequence Database, Aug. 4, 1999, XP002161433 Heidelberg DE Ac009100.

Meyerson M et al: "A family of human cc2–related protein kinases" EMBO Journal, GB, Oxford University Press, Surrey, vol. 11, No. 8, 1992, pp. 29019–2917 XP002128265, issn: 0261–4189, abstract; figure 1.

Waterston R.H.: "The sequence of *Homo sapiens* clone" EMBL Sequence Database, Sep. 5, 2000, XP002161434, Heidelberg DE Ac AC079615.

* cited by examiner

SEQUENCE LISTING

```
<160> NUMBER OF SEQ ID NOS: 13

<210> SEQ ID NO 1
<211> LENGTH: 561
<212> TYPE: DNA
<213> ORGANISM: homo sapiens

<400> SEQUENCE: 1
atggaaaagt atgaaaaatt agctaagact ggagaagggt cttatggggt tgtattcaaa      60
tgcagaaaca aaacctctgg acaagtagta gctgttaaaa aatttgtgga atctgaagat     120
gatcctgttg ttaagaaaat agcactaaga gaaatacgta tgttgaagca attaaaacat     180
ccaaatcttg tgaacctcat cgaggtgttc aggagaaaaa ggaaaatgca tttagttttt     240
gaatactgtg atcatacact tttaaatgag ctggaaagaa acccaaatgg agttgctgat     300
ggagtgatca aaagcgtatt atggcaaaca cttcaagctc ttaatttctg tcatatacat     360
aactgtattc acagagatat aaaacctgaa aatattctaa taactaagca aggaataatc     420
aagatttgtg acttcgggtt tgcacaaatt ctgagttgga cttcatcttt ctctggtgcc     480
tccttgattg gcttaatagt tgaccttctg aattcttttt ctgccaattc agagattttt     540
ctcctggctt ggatccattg c                                               561

<210> SEQ ID NO 2
<211> LENGTH: 187
<212> TYPE: PRT
<213> ORGANISM: homo sapiens

<400> SEQUENCE: 2

Met Glu Lys Tyr Glu Lys Leu Ala Lys Thr Gly Glu Gly Ser Tyr Gly
1               5                   10                  15

Val Val Phe Lys Cys Arg Asn Lys Thr Ser Gly Gln Val Val Ala Val
            20                  25                  30

Lys Lys Phe Val Glu Ser Glu Asp Asp Pro Val Val Lys Lys Ile Ala
        35                  40                  45

Leu Arg Glu Ile Arg Met Leu Lys Gln Leu Lys His Pro Asn Leu Val
    50                  55                  60

Asn Leu Ile Glu Val Phe Arg Arg Lys Arg Lys Met His Leu Val Phe
65                  70                  75                  80

Glu Tyr Cys Asp His Thr Leu Leu Asn Glu Leu Glu Arg Asn Pro Asn
```

```
                    85                  90                  95
Gly Val Ala Asp Gly Val Ile Lys Ser Val Leu Trp Gln Thr Leu Gln
                100                 105                 110

Ala Leu Asn Phe Cys His Ile His Asn Cys Ile His Arg Asp Ile Lys
            115                 120                 125

Pro Glu Asn Ile Leu Ile Thr Lys Gln Gly Ile Lys Ile Cys Asp
        130                 135                 140

Phe Gly Phe Ala Gln Ile Leu Ser Trp Thr Ser Phe Ser Gly Ala
145                 150                 155                 160

Ser Leu Ile Gly Leu Ile Val Asp Leu Leu Asn Ser Phe Ser Ala Asn
                165                 170                 175

Ser Glu Ile Phe Leu Leu Ala Trp Ile His Cys
            180                 185
```

<210> SEQ ID NO 3
<211> LENGTH: 1068
<212> TYPE: DNA
<213> ORGANISM: homo sapiens

<400> SEQUENCE: 3

```
atggaaaagt atgaaaaatt agctaagact ggagaagggt cttatggggt tgtattcaaa    60
tgcagaaaca aaacctctgg acaagtagta gctgttaaaa aatttgtgga atctgaagat   120
gatcctgttg ttaagaaaat agcactaaga gaaatacgta tgttgaagca attaaaacat   180
ccaaatcttg tgaacctcat cgaggtgttc aggagaaaaa ggaaaatgca tttagttttt   240
gaatactgtg atcatacact tttaaatgag ctggaaagaa acccaaatgg agttgctgat   300
ggagtgatca aaagcgtatt atggcaaaca cttcaagctc ttaatttctg tcatatacat   360
aactgtattc acagagatat aaaacctgaa atattctaa taactaagca aggaataatc   420
aagatttgtg acttcgggtt tgcacaaatt ctgattccag agatgccta caccgattat   480
gtagctacga gatggtaccg agctcctgaa cttcttgtgg agatactca gtatggttct   540
tcagtcgata tatgggctat tggttgtgtt tttgcagagc tcctgacagg ccagccactg   600
tggcctggaa atcagatgt ggaccaactt tatctgataa tcagaacact agtagagacg   660
gggtttcgcc atgttgacca ggctggtctc gaactcttga cgtcaagtga tccacctgcc   720
gtagcctctc aaagtgctgg aattacagga aaattaatcc caagacatca atcaatcttt   780
aaaagtaacg ggttttttcca tgcatcagt atacctgagc cagaagacat ggaaactctt   840
gaggaaaagt tctcagatgt tcatcctgtg gctctgaact tcatgaaggg gtgtctgaag   900
atgaatccag atgacagatt aacctgttcc caactcctgg agagctccta ctttgattct   960
tttcaagagg cccaaattaa agaaaagca cgtaatgaag gaagaaacag aagacgccaa  1020
caggtcagag gctgtgtttg gctgctgcag ctctgctcca ggctgcat                1068
```

<210> SEQ ID NO 4
<211> LENGTH: 356
<212> TYPE: PRT
<213> ORGANISM: homo sapiens

<400> SEQUENCE: 4

```
Met Glu Lys Tyr Glu Lys Leu Ala Lys Thr Gly Glu Gly Ser Tyr Gly
1               5                   10                  15

Val Val Phe Lys Cys Arg Asn Lys Thr Ser Gly Gln Val Val Ala Val
            20                  25                  30

Lys Lys Phe Val Glu Ser Glu Asp Asp Pro Val Val Lys Lys Ile Ala
```

```
             35                  40                  45
Leu Arg Glu Ile Arg Met Leu Lys Gln Leu Lys His Pro Asn Leu Val
     50                  55                  60

Asn Leu Ile Glu Val Phe Arg Arg Lys Arg Lys Met His Leu Val Phe
 65                  70                  75                  80

Glu Tyr Cys Asp His Thr Leu Leu Asn Glu Leu Glu Arg Asn Pro Asn
                 85                  90                  95

Gly Val Ala Asp Gly Val Ile Lys Ser Val Leu Trp Gln Thr Leu Gln
            100                 105                 110

Ala Leu Asn Phe Cys His Ile His Asn Cys Ile His Arg Asp Ile Lys
            115                 120                 125

Pro Glu Asn Ile Leu Ile Thr Lys Gln Gly Ile Ile Lys Ile Cys Asp
    130                 135                 140

Phe Gly Phe Ala Gln Ile Leu Ile Pro Gly Asp Ala Tyr Thr Asp Tyr
145                 150                 155                 160

Val Ala Thr Arg Trp Tyr Arg Ala Pro Glu Leu Leu Val Gly Asp Thr
                165                 170                 175

Gln Tyr Gly Ser Ser Val Asp Ile Trp Ala Ile Gly Cys Val Phe Ala
            180                 185                 190

Glu Leu Leu Thr Gly Gln Pro Leu Trp Pro Gly Lys Ser Asp Val Asp
        195                 200                 205

Gln Leu Tyr Leu Ile Ile Arg Thr Leu Val Glu Thr Gly Phe Arg His
    210                 215                 220

Val Asp Gln Ala Gly Leu Glu Leu Leu Thr Ser Ser Asp Pro Pro Ala
225                 230                 235                 240

Val Ala Ser Gln Ser Ala Gly Ile Thr Gly Lys Leu Ile Pro Arg His
                245                 250                 255

Gln Ser Ile Phe Lys Ser Asn Gly Phe Phe His Gly Ile Ser Ile Pro
            260                 265                 270

Glu Pro Glu Asp Met Glu Thr Leu Glu Glu Lys Phe Ser Asp Val His
        275                 280                 285

Pro Val Ala Leu Asn Phe Met Lys Gly Cys Leu Lys Met Asn Pro Asp
    290                 295                 300

Asp Arg Leu Thr Cys Ser Gln Leu Leu Glu Ser Ser Tyr Phe Asp Ser
305                 310                 315                 320

Phe Gln Glu Ala Gln Ile Lys Arg Lys Ala Arg Asn Glu Gly Arg Asn
                325                 330                 335

Arg Arg Arg Gln Gln Val Arg Gly Cys Val Trp Leu Leu Gln Leu Cys
            340                 345                 350

Ser Arg Leu His
        355

<210> SEQ ID NO 5
<211> LENGTH: 972
<212> TYPE: DNA
<213> ORGANISM: homo sapiens

<400> SEQUENCE: 5
atggaaaagt atgaaaaatt agctaagact ggagaagggt cttatggggt tgtattcaaa      60
tgcagaaaca aaacctctgg acaagtagta gctgttaaaa aatttgtgga atctgaagat     120
gatcctgttg ttaagaaaat agcactaaga gaaatacgta tgttgaagca attaaaacat     180
ccaaatcttg tgaacctcat cgaggtgttc aggagaaaaa ggaaaatgca tttagttttt     240
gaatactgtg atcatacact tttaaatgag ctggaaagaa acccaaatgg agttgctgat     300
```

```
ggagtgatca aaagcgtatt atggcaaaca cttcaagctc ttaatttctg tcatatacat    360
aactgtattc acagagatat aaaacctgaa aatattctaa taactaagca aggaataatc    420
aagatttgtg acttcgggtt tgcacaaatt ctgattccag gagatgccta caccgattat    480
gtagctacga gatggtaccg agctcctgaa cttcttgtgg agatactca gtatggttct     540 tcagtcgata tatgggctat tggttgtgtt tttgcagagc tcctgacagg ccagccactg    600
tggcctggaa aatcagatgt ggaccaactt tatctgataa tcagaacact aggaaaatta    660
atcccaagac atcaatcaat ctttaaaagt aacgggtttt ccatggcat cagtataccc    720 gagccagaag acatggaaac tcttgaggaa aagttctcag atgttcatcc tgtggctctg    780
aacttcatga aggggtgtct gaagatgaat ccagatgaca gattaacctg ttcccaactc    840
ctggagagct cctactttga ttcttttcaa gaggcccaaa ttaaaagaaa agcacgtaat    900
gaaggaagaa acagaagacg ccaacaggtc agaggctgtg tttggctgct gcagctctgc    960
tccaggctgc at                                                         972
```

```
<210> SEQ ID NO 6
<211> LENGTH: 324
<212> TYPE: PRT
<213> ORGANISM: homo sapiens

<400> SEQUENCE: 6

Met Glu Lys Tyr Glu Lys Leu Ala Lys Thr Gly Glu Gly Ser Tyr Gly
1               5                   10                  15

Val Val Phe Lys Cys Arg Asn Lys Thr Ser Gly Gln Val Val Ala Val
                20                  25                  30

Lys Lys Phe Val Glu Ser Glu Asp Asp Pro Val Val Lys Lys Ile Ala
            35                  40                  45

Leu Arg Glu Ile Arg Met Leu Lys Gln Leu Lys His Pro Asn Leu Val
        50                  55                  60

Asn Leu Ile Glu Val Phe Arg Arg Lys Arg Lys Met His Leu Val Phe
65                  70                  75                  80

Glu Tyr Cys Asp His Thr Leu Leu Asn Glu Leu Glu Arg Asn Pro Asn
                85                  90                  95

Gly Val Ala Asp Gly Val Ile Lys Ser Val Leu Trp Gln Thr Leu Gln
            100                 105                 110

Ala Leu Asn Phe Cys His Ile His Asn Cys Ile His Arg Asp Ile Lys
        115                 120                 125

Pro Glu Asn Ile Leu Ile Thr Lys Gln Gly Ile Ile Lys Ile Cys Asp
    130                 135                 140

Phe Gly Phe Ala Gln Ile Leu Ile Pro Gly Asp Ala Tyr Thr Asp Tyr
145                 150                 155                 160

Val Ala Thr Arg Trp Tyr Arg Ala Pro Glu Leu Leu Val Gly Asp Thr
                165                 170                 175

Gln Tyr Gly Ser Ser Val Asp Ile Trp Ala Ile Gly Cys Val Phe Ala
            180                 185                 190

Glu Leu Leu Thr Gly Gln Pro Leu Trp Pro Gly Lys Ser Asp Val Asp
        195                 200                 205

Gln Leu Tyr Leu Ile Ile Arg Thr Leu Gly Lys Leu Ile Pro Arg His
    210                 215                 220

Gln Ser Ile Phe Lys Ser Asn Gly Phe His Gly Ile Ser Ile Pro
225                 230                 235                 240

Glu Pro Glu Asp Met Glu Thr Leu Glu Glu Lys Phe Ser Asp Val His
```

```
            245                 250                 255
Pro Val Ala Leu Asn Phe Met Lys Gly Cys Leu Lys Met Asn Pro Asp
            260                 265                 270

Asp Arg Leu Thr Cys Ser Gln Leu Leu Glu Ser Ser Tyr Phe Asp Ser
            275                 280                 285

Phe Gln Glu Ala Gln Ile Lys Arg Lys Ala Arg Asn Glu Gly Arg Asn
            290                 295                 300

Arg Arg Arg Gln Gln Val Arg Gly Cys Val Trp Leu Leu Gln Leu Cys
305                 310                 315                 320

Ser Arg Leu His

<210> SEQ ID NO 7
<211> LENGTH: 594
<212> TYPE: DNA
<213> ORGANISM: homo sapiens

<400> SEQUENCE: 7
atggaaaagt atgaaaaatt agctaagact ggagaagggt cttatggggt tgtattcaaa      60
tgcagaaaca aaacctctgg acaagtagta gctgttaaaa aatttgtgga atctgaagat    120
gatcctgttg ttaagaaaat agcactaaga gaaatacgta tgttgaagca attaaaacat    180
ccaaatcttg tgaacctcat cgaggtgttc aggagaaaaa ggaaaatgca tttagttttt    240
gaatactgtg atcatacact tttaaatgag ctggaaagaa acccaaatgg agttgctgat    300
ggagtgatca aaagcgtatt atggcaaaca cttcaagctc ttaatttctg tcatatacat    360
aactgtattc acagagatat aaaacctgaa atattctaa taactaagca aggaataatc    420
aagatttgtg acttcggggtt tgcacaaatt ctgagttgga cttcatcttt ctctggtgcc    480
tccttgattg gcttaatagt tgaccttctg aattctttt ctgccaattc agagattttt    540
ctcctggctt ggatccattg ctggaaaatt aatcccaaga catcaatcaa tctt           594

<210> SEQ ID NO 8
<211> LENGTH: 198
<212> TYPE: PRT
<213> ORGANISM: homo sapiens

<400> SEQUENCE: 8

Met Glu Lys Tyr Glu Lys Leu Ala Lys Thr Gly Glu Gly Ser Tyr Gly
1               5                   10                  15

Val Val Phe Lys Cys Arg Asn Lys Thr Ser Gly Gln Val Val Ala Val
            20                  25                  30

Lys Lys Phe Val Glu Ser Glu Asp Asp Pro Val Val Lys Lys Ile Ala
        35                  40                  45

Leu Arg Glu Ile Arg Met Leu Lys Gln Leu Lys His Pro Asn Leu Val
    50                  55                  60

Asn Leu Ile Glu Val Phe Arg Arg Lys Arg Lys Met His Leu Val Phe
65                  70                  75                  80

Glu Tyr Cys Asp His Thr Leu Leu Asn Glu Leu Glu Arg Asn Pro Asn
                85                  90                  95

Gly Val Ala Asp Gly Val Ile Lys Ser Val Leu Trp Gln Thr Leu Gln
            100                 105                 110

Ala Leu Asn Phe Cys His Ile His Asn Cys Ile His Arg Asp Ile Lys
        115                 120                 125

Pro Glu Asn Ile Leu Ile Thr Lys Gln Gly Ile Ile Lys Ile Cys Asp
    130                 135                 140
```

Phe Gly Phe Ala Gln Ile Leu Ser Trp Thr Ser Phe Ser Gly Ala
145                 150                 155                 160

Ser Leu Ile Gly Leu Ile Val Asp Leu Leu Asn Ser Phe Ser Ala Asn
                165                 170                 175

Ser Glu Ile Phe Leu Leu Ala Trp Ile His Cys Trp Lys Ile Asn Pro
            180                 185                 190

Lys Thr Ser Ile Asn Leu
        195

<210> SEQ ID NO 9
<211> LENGTH: 1041
<212> TYPE: DNA
<213> ORGANISM: homo sapiens

<400> SEQUENCE: 9

| | | | | | |
|---|---|---|---|---|---|
| atggaaaagt | atgaaaaatt | agctaagact | ggagaagggt | cttatggggt | tgtattcaaa | 60 |
| tgcagaaaca | aaacctctgg | acaagtagta | gctgttaaaa | aatttgtgga | atctgaagat | 120 |
| gatcctgttg | ttaagaaaat | agcactaaga | gaaatacgta | tgttgaagca | attaaaacat | 180 |
| ccaaatcttg | tgaacctcat | cgaggtgttc | aggagaaaaa | ggaaaatgca | tttagttttt | 240 |
| gaatactgtg | atcatacact | tttaaatgag | ctggaaagaa | acccaaatgg | agttgctgat | 300 |
| ggagtgatca | aaagcgtatt | atggcaaaca | cttcaagctc | ttaatttctg | tcatatacat | 360 |
| aactgtattc | acagagatat | aaaacctgaa | aatattctaa | taactaagca | aggaataatc | 420 |
| aagatttgtg | acttcgggtt | tgcacaaatt | ctgattccag | agatgccta | caccgattat | 480 |
| gtagctacga | gatggtaccg | agctcctgaa | cttcttgtgg | agatactca | gtatggttct | 540 |
| tcagtcgata | tatgggctat | tggttgtgtt | tttgcagagc | tcctgacagg | ccagccactg | 600 |
| tggcctggaa | aatcagatgt | ggaccaactt | tatctgataa | tcagaacact | agtagagacg | 660 |
| gggtttcgcc | atgttgacca | ggctggtctc | gaactcttga | cgtcaagtga | tccacctgcc | 720 |
| gtagcctctc | aaagtgctgg | aattacagga | aaattaatcc | caagacatca | atcaatcttt | 780 |
| aaaagtaacg | ggttttttcca | tggcatcagt | atacctgagc | cagaagacat | ggaaactctt | 840 |
| gaggaaaagt | tctcagatgt | tcatcctgtg | gctctgaact | tcatgaaggg | gtgtctgaag | 900 |
| atgaatccag | atgacagatt | aacctgttcc | caactcctgg | agagctccta | ctttgattct | 960 |
| tttcaagagg | cccaaattaa | agaaaagca | cgtaatgaag | aagaaacag | aagacgccaa | 1020 |
| caggtacttc | cgctcaaaag | t | | | | 1041 |

<210> SEQ ID NO 10
<211> LENGTH: 347
<212> TYPE: PRT
<213> ORGANISM: homo sapiens

<400> SEQUENCE: 10

Met Glu Lys Tyr Glu Lys Leu Ala Lys Thr Gly Glu Gly Ser Tyr Gly
1               5                   10                  15

Val Val Phe Lys Cys Arg Asn Lys Thr Ser Gly Gln Val Val Ala Val
                20                  25                  30

Lys Lys Phe Val Glu Ser Glu Asp Asp Pro Val Val Lys Lys Ile Ala
            35                  40                  45

Leu Arg Glu Ile Arg Met Leu Lys Gln Leu Lys His Pro Asn Leu Val
        50                  55                  60

Asn Leu Ile Glu Val Phe Arg Arg Lys Arg Met His Leu Val Phe
65                  70                  75                  80

Glu Tyr Cys Asp His Thr Leu Leu Asn Glu Leu Glu Arg Asn Pro Asn
                85                  90                  95

Gly Val Ala Asp Gly Val Ile Lys Ser Val Leu Trp Gln Thr Leu Gln
            100                 105                 110

Ala Leu Asn Phe Cys His Ile His Asn Cys Ile His Arg Asp Ile Lys
            115                 120                 125

Pro Glu Asn Ile Leu Ile Thr Lys Gln Gly Ile Ile Lys Ile Cys Asp
        130                 135                 140

Phe Gly Phe Ala Gln Ile Leu Ile Pro Gly Asp Ala Tyr Thr Asp Tyr
145                 150                 155                 160

Val Ala Thr Arg Trp Tyr Arg Ala Pro Glu Leu Leu Val Gly Asp Thr
                165                 170                 175

Gln Tyr Gly Ser Ser Val Asp Ile Trp Ala Ile Gly Cys Val Phe Ala
            180                 185                 190

Glu Leu Thr Gly Gln Pro Leu Trp Pro Gly Lys Ser Asp Val Asp
            195                 200                 205

Gln Leu Tyr Leu Ile Ile Arg Thr Leu Val Glu Thr Gly Phe Arg His
        210                 215                 220

Val Asp Gln Ala Gly Leu Glu Leu Leu Thr Ser Ser Asp Pro Pro Ala
225                 230                 235                 240

Val Ala Ser Gln Ser Ala Gly Ile Thr Gly Lys Leu Ile Pro Arg His
                245                 250                 255

Gln Ser Ile Phe Lys Ser Asn Gly Phe Phe His Gly Ile Ser Ile Pro
            260                 265                 270

Glu Pro Glu Asp Met Glu Thr Leu Glu Glu Lys Phe Ser Asp Val His
        275                 280                 285

Pro Val Ala Leu Asn Phe Met Lys Gly Cys Leu Lys Met Asn Pro Asp
290                 295                 300

Asp Arg Leu Thr Cys Ser Gln Leu Leu Glu Ser Ser Tyr Phe Asp Ser
305                 310                 315                 320

Phe Gln Glu Ala Gln Ile Lys Arg Lys Ala Arg Asn Glu Gly Arg Asn
                325                 330                 335

Arg Arg Arg Gln Gln Val Leu Pro Leu Lys Ser
            340                 345

<210> SEQ ID NO 11
<211> LENGTH: 945
<212> TYPE: DNA
<213> ORGANISM: homo sapiens

<400> SEQUENCE: 11
atggaaaagt atgaaaaatt agctaagact ggagaagggt cttatggggt tgtattcaaa      60
tgcagaaaca aaacctctgg acaagtagta gctgttaaaa aatttgtgga atctgaagat     120
gatcctgttg ttaagaaaat agcactaaga gaaatacgta tgttgaagca attaaaacat     180
ccaaatcttg tgaacctcat cgaggtgttc aggagaaaaa ggaaaatgca tttagttttt     240
gaatactgtg atcatacact tttaaatgag ctggaaagaa acccaaatgg agttgctgat     300
ggagtgatca aaagcgtatt atggcaaaca cttcaagctc ttaatttctg tcatatacat     360
aactgtattc acagagatat aaaacctgaa atattctaa taactaagca aggaataatc     420
aagatttgtg acttcgggtt tgcacaaatt ctgattccag agatgcctac accgattat     480 gtagctacga gatggtaccg agctcctgaa cttcttgtgg gagatactca gtatggttct     540
tcagtcgata tatgggctat tggttgtgtt tttgcagagc tcctgacagg ccagccactg     600

-continued

```
tggcctggaa aatcagatgt ggaccaactt tatctgataa tcagaacact aggaaaatta    660
atcccaagac atcaatcaat ctttaaaagt aacgggtttt tccatggcat cagtatacct    720
gagccagaag acatggaaac tcttgaggaa agttctcag atgttcatcc tgtggctctg     780
aacttcatga agggtgtct gaagatgaat ccagatgaca gattaacctg ttcccaactc     840
ctggagagct cctactttga ttcttttcaa gaggcccaaa ttaaaagaaa agcacgtaat    900
gaaggaagaa acagaagacg ccaacaggta cttccgctca aaagt                    945
```

<210> SEQ ID NO 12
<211> LENGTH: 315
<212> TYPE: PRT
<213> ORGANISM: homo sapiens

<400> SEQUENCE: 12

```
Met Glu Lys Tyr Glu Lys Leu Ala Lys Thr Gly Glu Gly Ser Tyr Gly
1               5                   10                  15

Val Val Phe Lys Cys Arg Asn Lys Thr Ser Gly Gln Val Val Ala Val
                20                  25                  30

Lys Lys Phe Val Glu Ser Glu Asp Asp Pro Val Val Lys Lys Ile Ala
            35                  40                  45

Leu Arg Glu Ile Arg Met Leu Lys Gln Leu Lys His Pro Asn Leu Val
        50                  55                  60

Asn Leu Ile Glu Val Phe Arg Arg Lys Arg Met His Leu Val Phe
65                  70                  75                  80

Glu Tyr Cys Asp His Thr Leu Leu Asn Glu Leu Glu Arg Asn Pro Asn
                85                  90                  95

Gly Val Ala Asp Gly Val Ile Lys Ser Val Leu Trp Gln Thr Leu Gln
            100                 105                 110

Ala Leu Asn Phe Cys His Ile His Asn Cys Ile His Arg Asp Ile Lys
        115                 120                 125

Pro Glu Asn Ile Leu Ile Thr Lys Gln Gly Ile Lys Ile Cys Asp
130                 135                 140

Phe Gly Phe Ala Gln Ile Leu Ile Pro Gly Asp Ala Tyr Thr Asp Tyr
145                 150                 155                 160

Val Ala Thr Arg Trp Tyr Arg Ala Pro Glu Leu Leu Val Gly Asp Thr
                165                 170                 175

Gln Tyr Gly Ser Ser Val Asp Ile Trp Ala Ile Gly Cys Val Phe Ala
            180                 185                 190

Glu Leu Leu Thr Gly Gln Pro Leu Trp Pro Gly Lys Ser Asp Val Asp
        195                 200                 205

Gln Leu Tyr Leu Ile Ile Arg Thr Leu Gly Lys Leu Ile Pro Arg His
    210                 215                 220

Gln Ser Ile Phe Lys Ser Asn Gly Phe His Gly Ile Ser Ile Pro
225                 230                 235                 240

Glu Pro Glu Asp Met Glu Thr Leu Glu Glu Lys Phe Ser Asp Val His
                245                 250                 255

Pro Val Ala Leu Asn Phe Met Lys Gly Cys Leu Lys Met Asn Pro Asp
            260                 265                 270

Asp Arg Leu Thr Cys Ser Gln Leu Leu Glu Ser Ser Tyr Phe Asp Ser
        275                 280                 285

Phe Gln Glu Ala Gln Ile Lys Arg Lys Ala Arg Asn Glu Gly Arg Asn
    290                 295                 300

Arg Arg Arg Gln Gln Val Leu Pro Leu Lys Ser
```

305            310            315

<210> SEQ ID NO 13
<211> LENGTH: 1819
<212> TYPE: DNA
<213> ORGANISM: homo sapiens

<400> SEQUENCE: 13

| | | | | | |
|---|---|---|---|---|---|
| ctccgagcga | cacgcgcggg | agctggggct | ggggctgttc | ggcgctgctc | gaagcttcgt | 60 |
| caccgtcgcc | ctgtgggtgc | agtgcagcat | tgtactgcaa | gtcaatcgat | acaataattt | 120 |
| aagtcacttc | agctataatg | aaaagtatg | aaaaattagc | taagactgga | gaagggtctt | 180 |
| atggggttgt | attcaaatgc | agaaacaaaa | cctctggaca | agtagtagct | gttaaaaaat | 240 |
| ttgtggaatc | tgaagatgat | cctgttgtta | agaaaatagc | actaagagaa | atacgtatgt | 300 |
| tgaagcaatt | aaaacatcca | aatcttgtga | acctcatcga | ggtgttcagg | agaaaaagga | 360 |
| aaatgcattt | agtttttgaa | tactgtgatc | atacactttt | aaatgagctg | gaaagaaacc | 420 |
| caaatggagt | tgctgatgga | gtgatcaaaa | gcgtattatg | gcaaacactt | caagctctta | 480 |
| atttctgtca | tatacataac | tgtattcaca | gagatataaa | acctgaaaat | attctaataa | 540 |
| ctaagcaagg | aataatcaag | atttgtgact | tcgggtttgc | acaaattctg | agttggactt | 600 |
| catctttctc | tggtgcctcc | ttgattggct | taatagttga | ccttctgaat | tcttttctg | 660 |
| ccaattcaga | gattttctc | ctggcttgga | tccattgctg | acacagtgtt | tcaccatggg | 720 |
| gcccaggctc | atctcgaact | tctggcctca | agtgatcctt | ccacctcggc | ctcccaaagt | 780 |
| gctggattgc | aagtgtgagc | caccgtgccc | agccagattt | ttcaaacaat | aactactgag | 840 |
| agctcacaag | attgtttta | gtgggaacac | aatttcgaac | aaattcttga | aacgcattc | 900 |
| caggagatgc | ctacaccgat | tatgtagcta | cgagatggta | ccgagctcct | gaacttcttg | 960 |
| tgggagatac | tcagtatggt | tcttcagtcg | atatatgggc | tattggttgt | gttttgcag | 1020 |
| agctcctgac | aggccagcca | ctgtggcctg | gaaaatcaga | tgtggaccaa | ctttatctga | 1080 |
| taatcagaac | actagtagag | acggggtttc | gccatgttga | ccaggctggt | ctcgaactct | 1140 |
| tgacgtcaag | tgatccacct | gccgtagcct | ctcaaagtgc | tggaattaca | ggaaaattaa | 1200 |
| tcccaagaca | tcaatcaatc | tttaaaagta | acgggttttt | ccatggcatc | agtatacctg | 1260 |
| agccagaaga | catggaaact | cttgaggaaa | agttctcaga | tgttcatcct | gtggctctga | 1320 |
| acttcatgaa | ggggtgtctg | aagatgaatc | cagatgacag | attaacctgt | tcccaactcc | 1380 |
| tggagagctc | ctactttgat | tcttttcaag | aggcccaaat | taaaagaaaa | gcacgtaatg | 1440 |
| aaggaagaaa | cagaagacgc | caacaggtca | gaggctgtgt | ttggctgctg | cagctctgct | 1500 |
| ccaggctgca | ttgagaatcg | atttcgagtg | tcttctcatt | cagggaccca | gccaaggagc | 1560 |
| agctcatatg | ggaaatatgc | ccttctcatg | gcagaggccc | gaacttgaat | acctaatgtc | 1620 |
| tgtcaggagt | gacttccgct | caaaagttaa | agtgctataa | aaataattcc | ttttttgttt | 1680 |
| ttgrttggct | gccttcaaa | gtgagacaag | gtggacacca | agacctttca | tttgtactgg | 1740 |
| tgtagtgatt | gctagcttaa | taaatattgg | gaattgatgt | ataaaaccct | agactatgaa | 1800 |
| aatatcaaaa | aaaaaaaaa | | | | | 1819 |

HUMAN KINASE PROTEINS AND POLYNUCLEOTIDES ENCODING THE SAME

The present application claims the benefit of U.S. Provisional Application No. 60/156,511 which was filed on Sep. 28, 1999 and is herein incorporated by reference in its entirety.

1. INTRODUCTION

The present invention relates to the discovery, identification, and characterization of novel human polynucleotides encoding proteins that share sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring and the treatment of physiological disorders.

2. BACKGROUND OF THE INVENTION

Kinases mediate phosphorylation of a wide variety of proteins and compounds in the cell. Along with phosphatases, kinases are involved in a wide range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal kinases, and more particularly serine/threonine protein kinases. As such, the novel sequences represent a new family of proteins having homologues and orthologs across a range of phyla and species.

The novel human nucleic acid sequences described herein, encode alternative proteins/open reading frames (ORFs) of 187, 356, 324, 198, 347, and 315 amino acids in length (see SEQ ID NOS: 2, 4, 6, 8, 10, and 12).

The invention also encompasses agonists and antagonists of the described NHPs, including small molecules, large molecules, mutant NHPs, or portions thereof that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP sequences (e.g., expression constructs that place the described gene under the control of a strong promoter system). The present invention also includes both transgenic animals that express a NHP transgene, and NHP "knockouts" (which can be conditional) that do not express a functional NHP.

Further, the present invention also relates to processes for identifying compounds that modulate, i.e., act as agonists or antagonists, of NHP expression and/or NHP product activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of novel human ORFs that encode the described NHP kinase-like proteins.

5. DETAILED DESCRIPTION OF THE INVENTION

The NHPs, described for the first time herein, are novel proteins that are expressed in, inter alia, human cell lines, and human brain, pituitary, spinal cord, spleen, trachea, kidney, prostate, testis, and adrenal gland cells. The described sequences were compiled from gene trapped cDNAs, and human testis cDNA libraries, (Clontech, Palo Alto, Calif.).

The present invention encompasses the nucleotides presented in the Sequence Listing, host cells expressing such nucleotides, the expression products of such nucleotides, and: (a) nucleotides that encode mammalian homologs of the described sequences, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence in deleted; (d) nucleotides that encode chimeric fusion proteins containing all or a portion of a coding region of an NHP, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989., Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of SEQ ID NO:1 (as measured by BLAST sequence comparison analysis using, for example, the GCG sequence analysis package using default parameters).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length may partially overlap each other and/or the NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP sequence antisense molecules, useful, for example, in NHP sequence regulation (for and/or as antisense primers in amplification reactions of NHP gene nucleic acid sequences). With respect to NHP sequence regulation, such techniques can be used to regulate biological functions. Further, such sequences can be used as part of ribozyme and/or triple helix sequences that are also useful for NHP sequence regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP sequence homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of MRNA prepared from, for example, human or non-human cell lines or tissue, such as prostate, rectum, colon, or adrenal gland, known or suspected to express an allele of a NHP gene. The PCR product can be subcloned and sequenced to ensure that the amplified sequences represent the sequence of the desired NHP. The PCR fragment can then be used to isolate a full length cDNA clone by a variety of methods. For example, the amplified fragment can be labeled and used to screen a CDNA library, such as a bacteriophage CDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP sequence, such as, for example, testis tissue). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutations) responsible for the loss or alteration of function of the mutant NHP sequence product can be ascertained.

Alternatively, a genomic library can be constructed using DNA obtained from an individual suspected of or known to carry a mutant NHP allele (e.g., a person manifesting a NHP-associated phenotype such as, for example, immune disorders, obesity, high blood pressure, etc.), or a cDNA library can be constructed using RNA from a tissue known, or suspected, to express a mutant NHP allele. A:normal NHP sequence, or any suitable fragment thereof, can then be labeled and used as a probe to identify the corresponding mutant NHP allele in such libraries. Clones containing mutant NHP sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous;:NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include, but are not limited to, the human cytomegalovirus (hCMV) immediate early gene, regulatable, viral elements (particularly retroviral LTR promoters) the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic proteins, expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of the NHP, as well as compounds or nucleotide constructs that inhibit expression of a NHP sequence (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers,. etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding the NHPS, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. The NHP nucleotide sequences were obtained from human cDNA libraries using probes and/or primers generated from human gene trapped sequence tags.

Expression analysis has provided evidence that the described NHPs can be expressed in human tissues as well as gene trapped human cells. In addition to the serine/threonine kinases, the described NHPs also share significant similarity to a range of additional kinase families such as cell division protein kinases, cyclin dependent kinase, etc. from a range of phyla and species. Given the physiological importance of protein kinases, they have been subject to intense scrutiny as exemplified and discussed in U.S. Pat. No. 5,817,479 herein incorporated by reference in its entirety.

During the generation of the described sequences, a polymorphism was identified in the 3' UTR reported in SEQ ID NO:13 (which includes a complete NHP ORF flanked by 5' and 3' sequences.

5.2 NHPS and NHP Polypeptides

NHPs, polypeptides, peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be as pharmaceutical reagents useful in the therapeutic treatment of mental, biological, or medical disorders and disease.

The Sequence Listing discloses the amino acid sequences encoded by the described NHP sequences. The NHPs have initiator methionines in DNA sequence contexts consistent with eucaryotic translation initiation sites.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., i E. coli, B. subtilis) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the E. coli expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like., PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus (AcNPV) is used as a vector to express foreign genes. The virus grows in Spodoptera frugiperda cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, eg., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP sequence or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetaboiite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns and histidine-tagged proteins are selectively eluted with imidazole-containing buffers.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP sequence product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding the a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxoid or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP sequence products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')₂ fragments which can be produced by pepsin digestion of the antibody molecule and the Fab fragments which can be generated by reducing the disulfide bridges of the F(ab')₂ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising the nucleotide sequence of SEQ ID NO:9.

2. An isolated nucleic acid molecule comprising a nucleotide sequence that:
   (a) encodes the amino acid sequence shown in SEQ ID NO:10; and
   (b) hybridizes under stringent conditions to the nucleotide sequence of SEQ ID NO:9 or the complement thereof.

3. An isolated nucleic acid molecule comprising a nucleotide sequence encoding the amino acid sequence shown in SEQ ID NO:12.

4. The isolated nucleic acid molecule of claim 3, wherein said molecule comprises the nucleotide sequence of SEQ ID NO:11.

5. A recombinant expression vector comprising the isolated nucleic acid molecule of claim 2.

6. The expression vector of claim 5, wherein said vector comprises the nucleotide sequence of SEQ ID NO:9.

7. A recombinant expression vector comprising the isolated nucleic acid molecule of claim 3.

8. The expression vector of claim 7, wherein said vector comprises the nucleotide sequence of SEQ ID NO:11.

9. A host cell comprising the expression vector of claim 5.

10. A host cell comprising the expression vector of claim 7.

* * * * *